US010914714B2

(12) United States Patent
Salinas et al.

(10) Patent No.: US 10,914,714 B2
(45) Date of Patent: Feb. 9, 2021

(54) FACILITATION OF CANINE DETECTION OF ILLEGAL SUBSTANCES IN VEHICLES

(71) Applicants: Luis E. Salinas, Laramie, WY (US); Edward J. Maxwell, Yarmouth, ME (US)

(72) Inventors: Luis E. Salinas, Laramie, WY (US); Edward J. Maxwell, Yarmouth, ME (US)

(*) Notice: Subject to any disclaimer, the term of this patent is extended or adjusted under 35 U.S.C. 154(b) by 114 days.

(21) Appl. No.: 16/148,781

(22) Filed: Oct. 1, 2018

(65) Prior Publication Data

US 2020/0103384 A1    Apr. 2, 2020

(51) Int. Cl.
| | |
|---|---|
| *G01N 33/00* | (2006.01) |
| *A01K 1/00* | (2006.01) |
| *G01N 1/00* | (2006.01) |
| *G01N 23/04* | (2018.01) |
| *G01N 30/72* | (2006.01) |
| *E04H 6/42* | (2006.01) |

(52) U.S. Cl.
CPC ....... *G01N 33/0001* (2013.01); *A01K 1/0052* (2013.01); *A01K 1/0064* (2013.01); *E04H 6/42* (2013.01); *G01N 1/00* (2013.01); *G01N 23/04* (2013.01); *G01N 30/7206* (2013.01); *G01N 2001/002* (2013.01)

(58) Field of Classification Search
CPC .... G01N 1/00; G01N 2001/002; G01N 23/04; G01N 30/7206; G01N 33/0001; A01K 1/0047; A01K 1/0052; A01K 1/0058; A01K 1/0064; A01K 1/007; E04H 6/42

USPC ......... 73/23.2, 23.34, 23.42, 863.41, 863.71, 73/864.33
See application file for complete search history.

(56) References Cited

U.S. PATENT DOCUMENTS

| | | |
|---|---|---|
| 4,202,200 A | 5/1980 | Ellson |
| 4,580,440 A | 4/1986 | Reid et al. |
| 4,718,268 A | 1/1988 | Reid et al. |
| 5,345,809 A | 9/1994 | Corrigan et al. |
| 5,395,589 A | 3/1995 | Nacson |
| 5,859,362 A | 1/1999 | Neudorfl et al. |

(Continued)

OTHER PUBLICATIONS

F. Kiong "Vehicle Undercarriage Scanning System" https://eprints.usq.edu.au/536/1/FrederickCHONGchuenkiong-2005.pdf—submitted Oct. 27, 2005.

(Continued)

*Primary Examiner* — William V Gilbert

(57) ABSTRACT

A system includes a container to enclose vehicles within a chamber, an enclosed structure to house a canine to perform odor detection, and an air duct positioned therebetween. The container includes a first door, a second door, and a raised floor. The raised floor includes a first ramp leading to the first door, a second ramp leading to the second door, and sets of vent ducts defined between an outer wall and a top wall of the raised floor, the sets of vent ducts to direct air flow upwardly into the chamber of the container. The air duct includes a proximal end located proximate to an opening within the top wall of the container, a distal end fed through the enclosed structure to a canine-sniffing location, and one or more fan to pull air out of the chamber and deliver the air to the canine-sniffing location within the enclosed structure.

20 Claims, 11 Drawing Sheets

(56) References Cited

U.S. PATENT DOCUMENTS

| | | | |
|---|---|---|---|
| 5,915,268 A * | 6/1999 | Linker | G01N 1/24 422/93 |
| 6,067,167 A | 5/2000 | Atkinson et al. | |
| 6,085,601 A | 7/2000 | Linker et al. | |
| 6,610,977 B2 | 8/2003 | Megerle | |
| 6,848,325 B2 | 2/2005 | Parmeter et al. | |
| 6,972,693 B2 | 12/2005 | Brown | |
| 7,037,030 B2 | 5/2006 | McLemore | |
| 7,357,043 B2 | 4/2008 | Cumming et al. | |
| 7,913,540 B2 | 3/2011 | Brasfield | |
| 7,942,033 B2 | 5/2011 | Jenkins | |
| 8,561,486 B2 | 10/2013 | Novosselov et al. | |
| 8,701,463 B2 * | 4/2014 | Brasfield | G01N 33/0057 73/23.34 |
| 8,806,914 B2 | 8/2014 | Brasfield | |
| 8,881,574 B2 | 11/2014 | Saaski | |
| 8,931,327 B2 * | 1/2015 | Pearce | A01K 15/02 73/23.34 |
| 9,048,076 B2 | 6/2015 | Stott et al. | |
| 2004/0226342 A1 | 11/2004 | Taricco | |
| 2007/0056396 A1 * | 3/2007 | Mawer | G01N 27/622 73/866 |
| 2008/0053252 A1 * | 3/2008 | Jenkins | G01N 1/22 73/864.33 |
| 2009/0038555 A1 * | 2/2009 | Reese | A01K 15/02 119/174 |
| 2009/0155926 A1 | 6/2009 | Ovadia et al. | |
| 2009/0320620 A1 | 12/2009 | Hu et al. | |
| 2012/0103060 A1 * | 5/2012 | Brasfield | G01N 1/24 73/23.34 |
| 2017/0261478 A1 * | 9/2017 | Stokes | G01N 33/0001 |

OTHER PUBLICATIONS https://www.rapiscansystems.com/en/products/ase-z-portal-for-passenger-vehicles. Retrieved Oct. 1, 2018.

https://www.smithsdetection.com/index.php?option=com_k2&view=item&id=396&Itemid=600#.WefbgkwZOb8—Border screening technology for light vehicles. Retrieved Oct. 1, 2018.

M. Staymates et al., "Biomimetic Sniffing Improves the Detection Performance of a 3D Printed Nose of a Dog and a Commercial Trace Vapor Detector" https://www.rapiscansystems.com/en/products/cvi/ase_z_portal_for_passenger_vehicles—Passenger vehicle scanning system. Published: Dec. 1, 2016.

R. Ewing et al., "Direct Real-Time Detection of Vapors from Explosive Compounds" Anal. Chem., 2013, 85 (22), pp. 10977-10983, Publication Date (Web): Oct. 3, 2013.

Miny Young, "Evaluation of Non-Contact Sampling and Detection of Explosives" http://digitalcommons.fiu.edu/cgi/viewcontent.cgi?article=2109&context=etd. Retrieved Oct. 1, 2018.

* cited by examiner

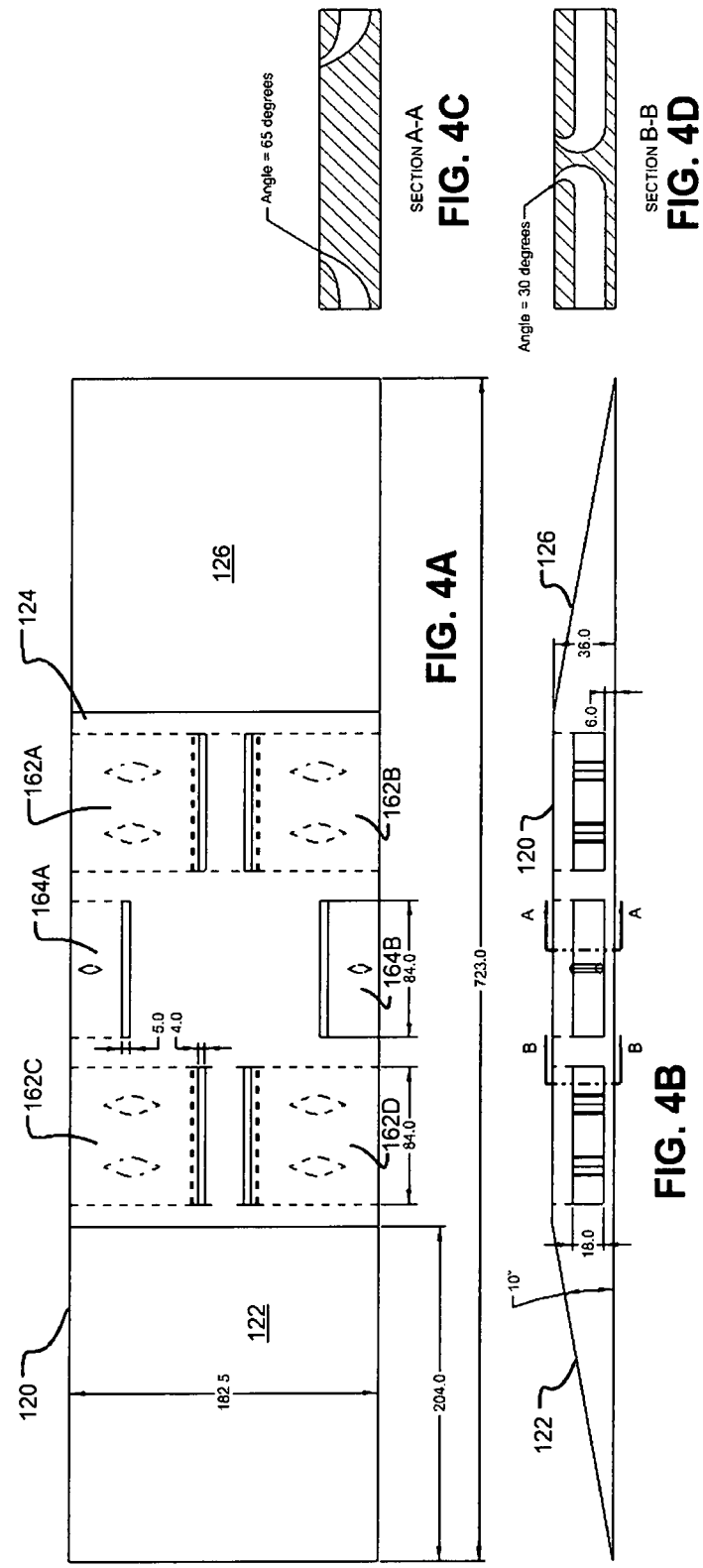

FACILITATION OF CANINE DETECTION OF ILLEGAL SUBSTANCES IN VEHICLES

BACKGROUND

A concern regarding Military Working Dogs (MWDs) and Police K9s is heat exhaustion. In 2016 alone, eleven Police K9s died due to heat exhaustion. The same year, heat exhaustion was cited as the number two cause of non-hostile action death in police dogs. It has become an issue of concern in both military and police K9 units, not only causing fatalities, but numerous injuries leading to potentially increased susceptibility to further injury or death. When temperatures are in excess of 86° F., 15 minutes is considered the upper limit of a work period, followed by rest periods of at least 40 minutes. At the southern United States border crossings, where this temperature is often exceeded, this leads to an extreme loss in efficiency in screening vehicles for illegal substances by canines.

BRIEF DESCRIPTION OF THE DRAWINGS

Various exemplary implementations of the present disclosure will be understood more fully from the detailed description given below and from the accompanying drawings of various exemplary implementations of the disclosure.

FIG. 4A is a top view of the raised floor of the container of FIG. 1A according to an embodiment.

FIG. 4B is a side view of the raised floor of the container of FIG. 1A according to an embodiment.

FIG. 4C is a cross-section view at section C-C of the raised floor of FIG. 4B according to an embodiment.

FIG. 4D is a cross-section view at section B-B of the raised floor of FIG. 4B.

DETAILED DESCRIPTION

Figure 1A:
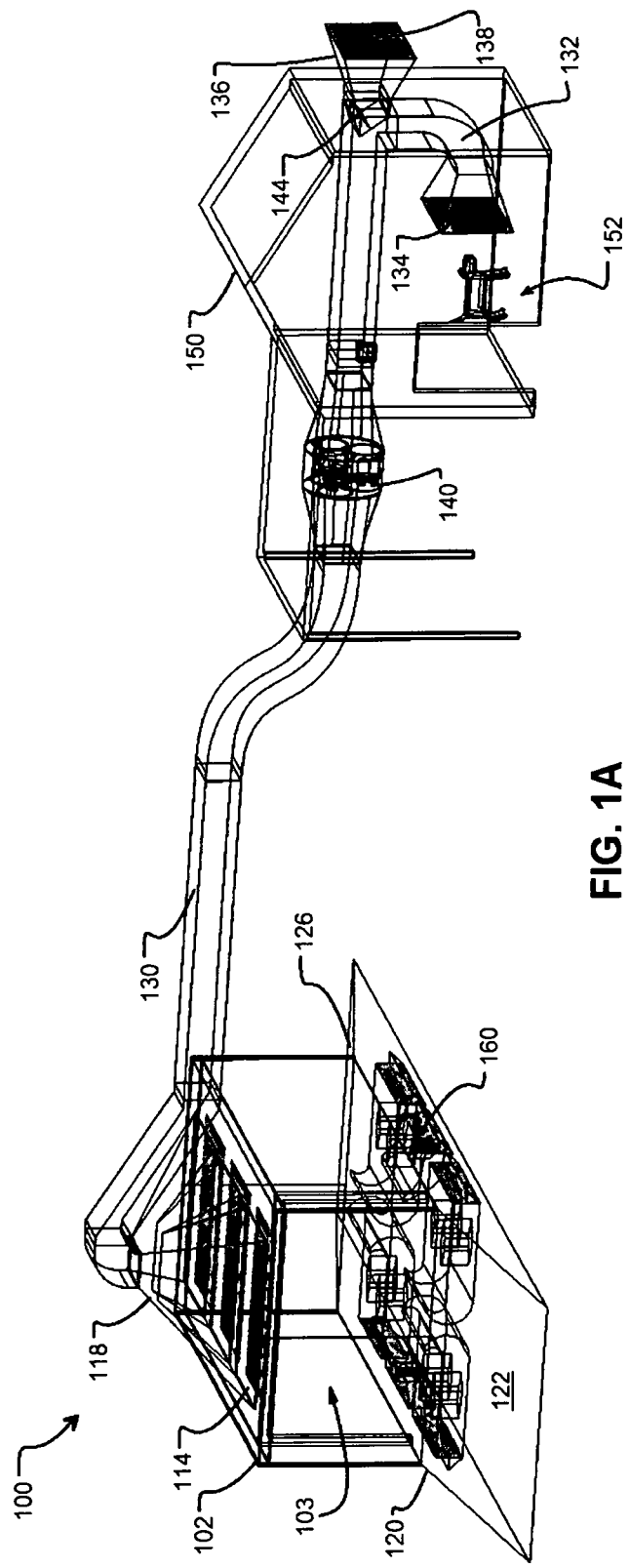
FIG. 1A is a perspective view of a system to facilitate canine detection of illegal substances in a vehicle according to an embodiment.

The disclosed system offers a solution to unnecessary heat injuries affecting border patrol K9s. Rather than having K9s patrol amongst vehicles approaching the border, K9s may be stationed in an air-conditioned room with their handler and have the aromas of vehicles brought to them. This could almost completely eliminate the risks associated with heat illness affecting K9s when searching vehicles for illegal substances, while maintaining the K9s role in the search. It would also prevent officers and K9s from wandering through lanes of traffic at the border; this is both tiring and inefficient, due to the large number of cars and the many fumes traveling in the air, and may also mask some aromas.

The southern United States border with Mexico would be a suitable location to employ the disclosed system, although it may be employed at other borders, at exits from reservations, or other entrances, including military and government, for example. Illegal smuggling of drugs, weapons, and explosives, as well as human trafficking, takes place at borders every day. In the Drug Enforcement Administration's 2016 National Drug Threat Assessment, it was stated, "The most common method employed by Mexican TCOs [Transnational Criminal Organizations] involves transporting drugs in vehicles through U.S. ports of entry (POEs). Illicit drugs are smuggled into the United States in concealed compartments within passenger vehicles or commingled with legitimate goods on tractor trailers." The U.S. Department of the Treasury has estimated drug trafficking to be a $64 billion yearly business in the U.S. K9s have proven their effectiveness in the search for these illegal substances: In fiscal year 2015, Customs and Border Protections K9 teams were responsible for the seizure of over $74 million in combined narcotics and currency busts.

The disclosed system is to help canines be more effective at detection by isolating the canines with the odors that need detection, as well as more efficient and productive in being able to work longer periods of time without rest. In various embodiments, the canine (or dog or other detection animal) is located within an enclosed structure that may be air conditioned and the odor-containing air is circulated to the canine.

More specifically, in one embodiment, the system includes a container to enclose vehicles within a chamber that are to be screened, an enclosed structure to house a canine to perform odor detection, and an air duct positioned therebetween. The container may include a first door at an entrance, a second door at an exit, and a raised floor. The raised floor may include a first ramp leading to the first door, a second ramp leading to the second door, and sets of vent ducts defined between at least one outer wall and a top wall of the raised floor. The sets of vent ducts may direct air flow upwardly into the chamber of the container. The air duct may include a proximal end located proximate to an opening within the top wall (or a side wall) of the container, a distal end fed through the enclosed structure to a canine-sniffing location, and one or more fan to pull air out of the chamber and deliver the air to the canine-sniffing location within the enclosed structure. Additional and alternative features will be discussed in more detail with reference to the various Figures.

Advantages of the disclosed system and present design include making the flow of air naturally accelerated, in lieu of using compressors, by way of vent ducts within the raised floor, to increase effectiveness of stirring up aromatic particles. Filters and screens (e.g., a screen-filter combination) for inlets to the vent ducts may prevent foreign object debris (FOD) from entering the chamber. The use of multiple fans may increase the volumetric flow rate, speeding up the process for each vehicle, while still being able to use affordable fans. The system design provides sufficient space to integrate an optional x-ray device and/or a gas-chromatograph mass-spectrometer device, to provide for x-ray scanning of the vehicle and redundant testing to detect illegal substances within or on the vehicle. The chamber may be of a size sufficient to isolate vehicles outside of the wind and exhaust of a typical traffic stop, making it easier for K9s to distinguish smells between each vehicle. Further, the K9s may remain within an air-conditioned building during the screening, preventing heat injury and exhaustion, thus boosting performance and effectiveness. In one embodiment, all the vehicles are processed through the system rather than only certain vehicles at random.

FIG. 1A is a perspective view of a system 100 to facilitate canine detection of illegal substances in a vehicle according to an embodiment. The system 100 may include a container 102 to enclose vehicles within a chamber that are to be screened, an enclosed structure 150 to house a canine to perform odor detection, and an air duct 130 positioned between the container 102 and the enclosed structure 150. The container 102 defines a chamber 103 which is to trap odors and particles to be sucked out by the air duct 130 into the enclosed structure 150. In one embodiment, the chamber 103 may be about 15 feet wide, 26 feet long, and 9 feet high, which is sized to fit the largest commercially available vehicles, such as Ford® F-series trucks. The chamber could, in other embodiments, be scaled for smaller lanes or vehicles, to enable quicker processing of smaller vehicles.

In various embodiments, the container 102 two side walls, a top wall, and a raised floor 120. The raised floor 120 may include a first ramp 122 leading to an entrance, a second ramp 126 leading to an exit, and sets of vent ducts 160 defined between outer walls of the raised floor 120 and a top wall of the raised floor. In this way, the sets of vent ducts 160 may direct air flow, from outside the container, upwardly into the chamber 103 of the container, past the vehicle, disturbing and dislodging air particles on the vehicle that may carry odors. The container 102 may further include an opening 114 (or multiple openings) within one of a sidewall or the top wall (as illustrated), out of which the directed air flow may exit into the air duct 130.

In various embodiments, the air duct 130 may include a proximal end that is proximate to the opening 114 of the container 102. In some embodiments, the proximal end of the air duct 130 is a pyramid-shaped funnel 118 positioned over the opening, to funnel the air from the chamber 103 into the air duct 130. The air duct 130 may further include one or more fan 140 located within the air duct 130 between the container 102 and the enclosed structure 150, to pull air from the chamber 103 to a canine-sniffing location 152 of the enclosed structure.

Additionally, a distal end of the air duct 130 may include a first portion 132 that is fed to the canine-sniffing location 152 inside of the enclosed structure 150. The distal end of the air duct 130 may further include a second portion 136 that exits the enclosed structure 136 and may be used to purge the air out of the chamber 103 and the air duct 130 in between screenings of different vehicles. The first portion 132 and the second portion 136 may include a first diffuser 134 and a second diffuser 138, respectively, to slow down the air before it exits the distal end of the air duct 130. In one embodiment, each diffuser 134 and 138 may cover an outlet with a square foot area of 24 square feet, e.g., 4 feet by 6 feet, but other dimensions are envisioned. Each diffuser 134 and 138 may also slow down the velocity of the air to between 2.25 miles per hour (mph) to 10 mph.

In various embodiments, the distal end of the air duct 130 may further include a pivotal flap 144 that may rotate (or pivot) between opening the first portion 132 to the air in the air duct and opening the second portion 136 to purge the air from the chamber 103 and the air duct 130. When the first portion 132 is open, the pivotal flap 144 may close the second portion 138. When the second portion 136 is open, the pivotal flap 144 may close the first portion 132.

Figure 1B:
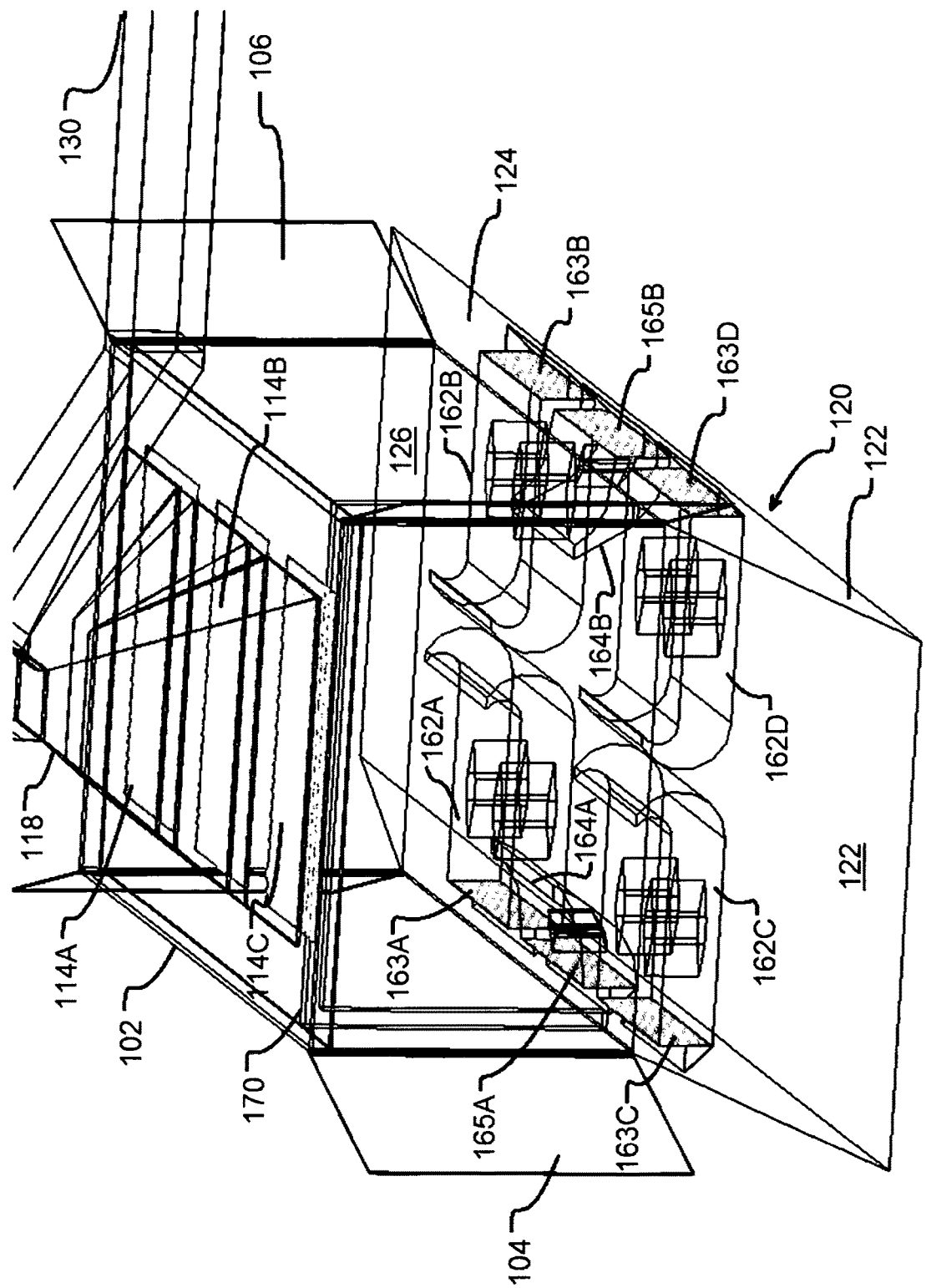
FIG. 1B is a front perspective view of the container of the system of FIG. 1A, according to an embodiment.

FIG. 1B is a front perspective view of the container 102 of the system 100 of FIG. 1A, according to an embodiment. The container 102, in alternative embodiments, may include a first door 104 (or set of first doors) to seal close the entrance of the container 102, and a second door 106 (or set of second doors) to seal close the exit of the container 102. The opening 114 of the container may further include multiple openings containing, respectively, a first grate 114A, a second grate 114B, and a third 144C, although fewer or more than three openings is envisioned. The pyramid-shaped funnel 118 positioned over the multiple openings may include a pyramid-shaped funnel that hovers over each grate 114A, 114B, and 114C.

The container 102 may further include an optional x-ray device 170 attached to upper sides of the chamber near one of the first door 104 or the second door 106. Illustrated is a slot for receipt of x-ray film, but this slot may represent the general location of the rest of the x-ray device 170 used to scan vehicles with x-rays. The x-ray device 170 may be sized to enable taking an x-ray of the vehicle as an additional method of detecting compartments or other objects that could hide contraband, drugs, trafficked humans, and the like, which will be discussed in more detail with reference to FIG. 3B.

The raised floor 120 may further include a middle portion 124 in which are located the sets of vent ducts 160. More specifically, the sets of vent ducts 160 may include a first vent duct 162A located between a first outer wall and a top wall of the raised floor 120. In various embodiments, the first vent duct 162A exits into the chamber 103 at an angle between 25 and 40 degrees (e.g., 30 degrees, for example) with respect to a top of the raised floor. The sets of vent ducts 160 may include a second vent duct 164A located between the first outer wall and the top wall of the raised floor 120. In embodiments, the second vent duct 164A exits into the chamber 103 at an angle between 55 and 75 degrees (e.g., 65 degrees, for example) with respect to a top of the raised floor. A third vent duct 162B may be located between a second outer wall and the top wall of the raised floor 120. In embodiments, the third vent duct 162B exits into the chamber 103 at an angle between 25 and 40 degrees and is positioned across the chamber 103 from the first vent duct 162A. A fourth vent duct 164B may be located between the second outer wall and the top wall of the raised floor 120. In embodiments, the fourth vent duct 164B exits into the chamber at an angle between 55 and 75 degrees and is positioned across the chamber 103 from the second vent duct 164A. Additional vent ducts are envisioned, for example, a fifth vent duct 162C similar to the first vent duct 162A and a sixth vent duct 162D similar to the third vent duct 162B, located on opposite sides of the chamber 103.

In various embodiments, each vent duct includes a screen-filter combination to protect against foreign object debris from entering the chamber 103. For example, each of the first, second, third, fourth, fifth, and sixth vent ducts 162A, 164A, 162B, 164B, 162C, and 162D include a first, second, third, fourth, fifth, and sixth screen-filter combinations 163A, 165A, 163B, 165B, 163C, and 163D, respectively. Furthermore, each vent duct of the sets of vent ducts 160 may include a diamond-shaped support to provide strength against collapse under the weight of the vehicles being screened. In one embodiment, the air enters the vent ducts at between one and four mph, and exits into the chamber at between four and 16 mph.

These vent ducts 162A, 164A, 162B, 164B, 162C, and 162D are arranged and blow air from the bottom of the chamber 103 upwardly towards the top of the chamber 103 at multiple angles, as discussed above, to be able to dislodge particles that carry odors from different parts of the vehicle. The moving air may then carry these particles through the grates 114A, 114B, and 114C into the air duct 130.

Figure 2A:
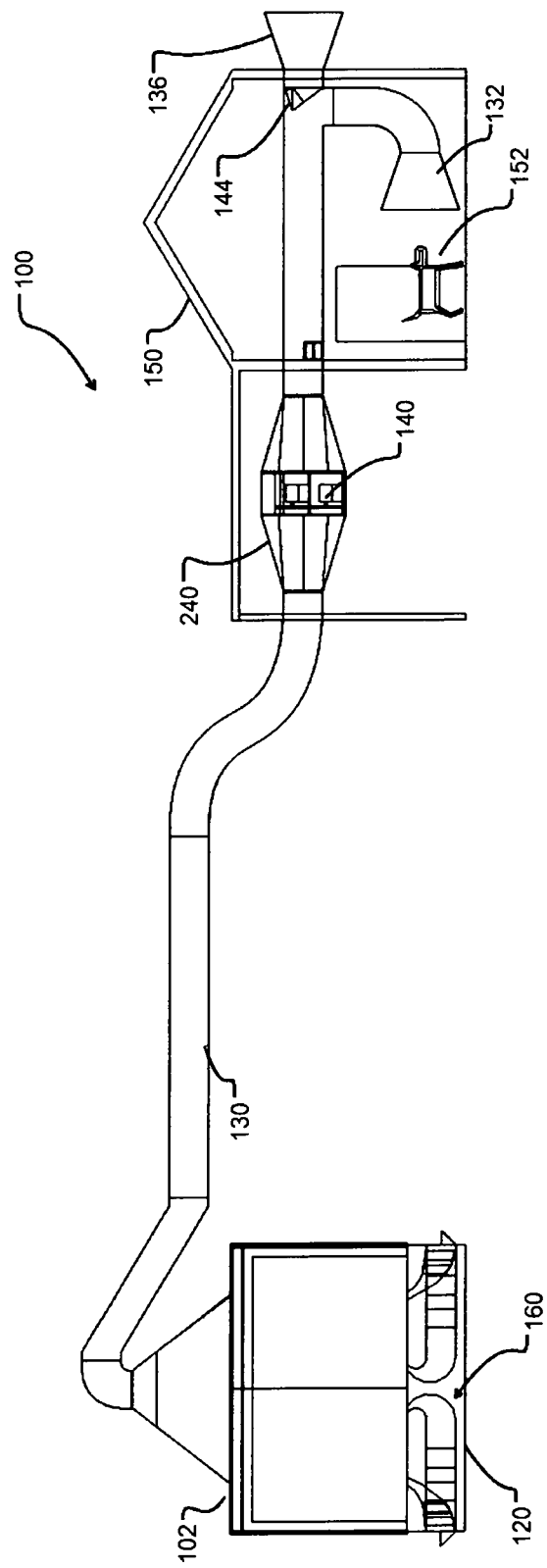
FIG. 2A is a side view of the system of FIG. 1A, illustrating air flow according to an embodiment.

FIG. 2A is a side view of the system 100 of FIG. 1A, illustrating air flow according to an embodiment. The air duct 130 may further include a fan housing 240 in which is located the one or more fan 140. The air flow is summarized as discussed above. After the one or more fan 140 is turned on, the air is pulled from the outside through the vent ducts 162A, 164A, 162B, 164B, 162C, and 162D located within the raised floor 120, and into the chamber 103. The air flow exiting the vent ducts may do so in a crisscross manner to generate maximum air turbulence and particular dislodgement. The air flow may then be directed to the ceiling (or toward a side in an alternative embodiment) where the openings in the container 102 are covered with the proximal end (the pyramid-shaped funnel 118) of the air duct 130. The difference in pressure created by the force of the one or more fan 140 pulls the air through the air duct 130 and into the distal end of the air duct 130.

In the illustrated embodiment, the pivotal flap 144 has been rotated to close the second portion 136 of the distal end and to direct the air through the first portion 132 of the distal end of the air duct 130. The air therefore is to exit into the canine-sniffing location 152 of the enclosed structure 150, e.g., a separate building or shack that may be air conditioned or otherwise cooled to care for the canine, helping the canine be more efficient and work a longer period of time without rest. After the vehicle exits the container 102, the pivotal flap 144 may be rotated to cover the entrance to the first portion 132 of the distal end, thus opening the second portion 136 of the distal end of the air duct 130 to purge the container 102 and the air duct 130 before screening another vehicle.

Figure 2B:
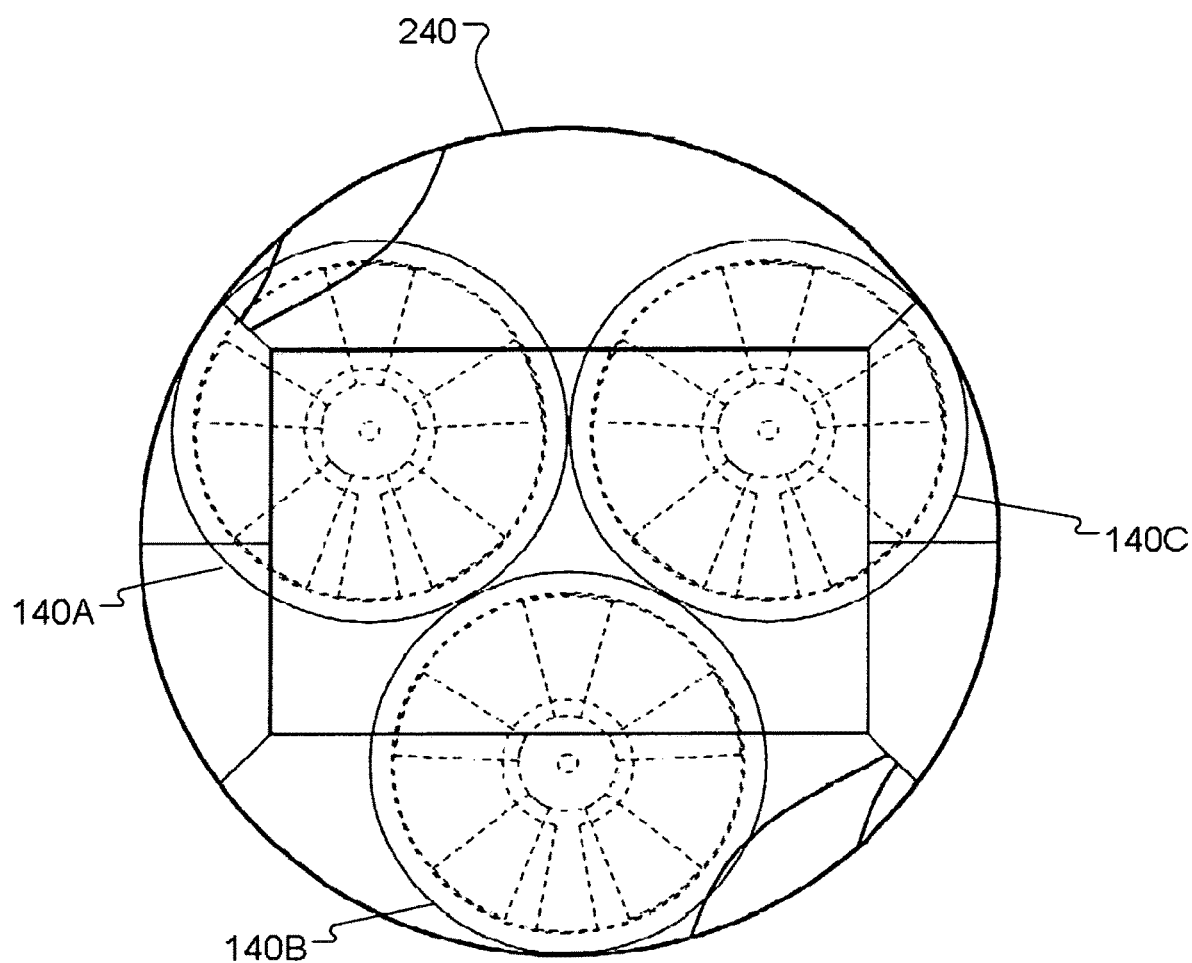
FIG. 2B is an enlarged front view of a set of fans used to generate the air flow described in FIG. 2A, according to an embodiment.

FIG. 2B is an enlarged front view of the housing 240 and the set of fans within the housing 240 used to generate the air flow described in FIG. 2A, according to an embodiment. In the embodiment of FIG. 2B, the set of fans includes a first fan 140A, a second fan 140B, and a third fan 140C, e.g., a set of three fans arranged in parallel. In one embodiment, each of the first, second, and third fans 140A, 140B, and 140C may be an AID210 fan, by Continental Fan Manufacturing of Buffalo, N.Y., each of which may move between 1600 and 7000 cubic feet of air per minute. The three fans 140A, 140B, and 140C of this type of fan may together pull between 4,800 cubic feet per minute and 21,000 cubic feet per minute (cfm) of the air. At this rate, the three fans run a full cycle of the chamber volume within 10 seconds.

Figure 3A:
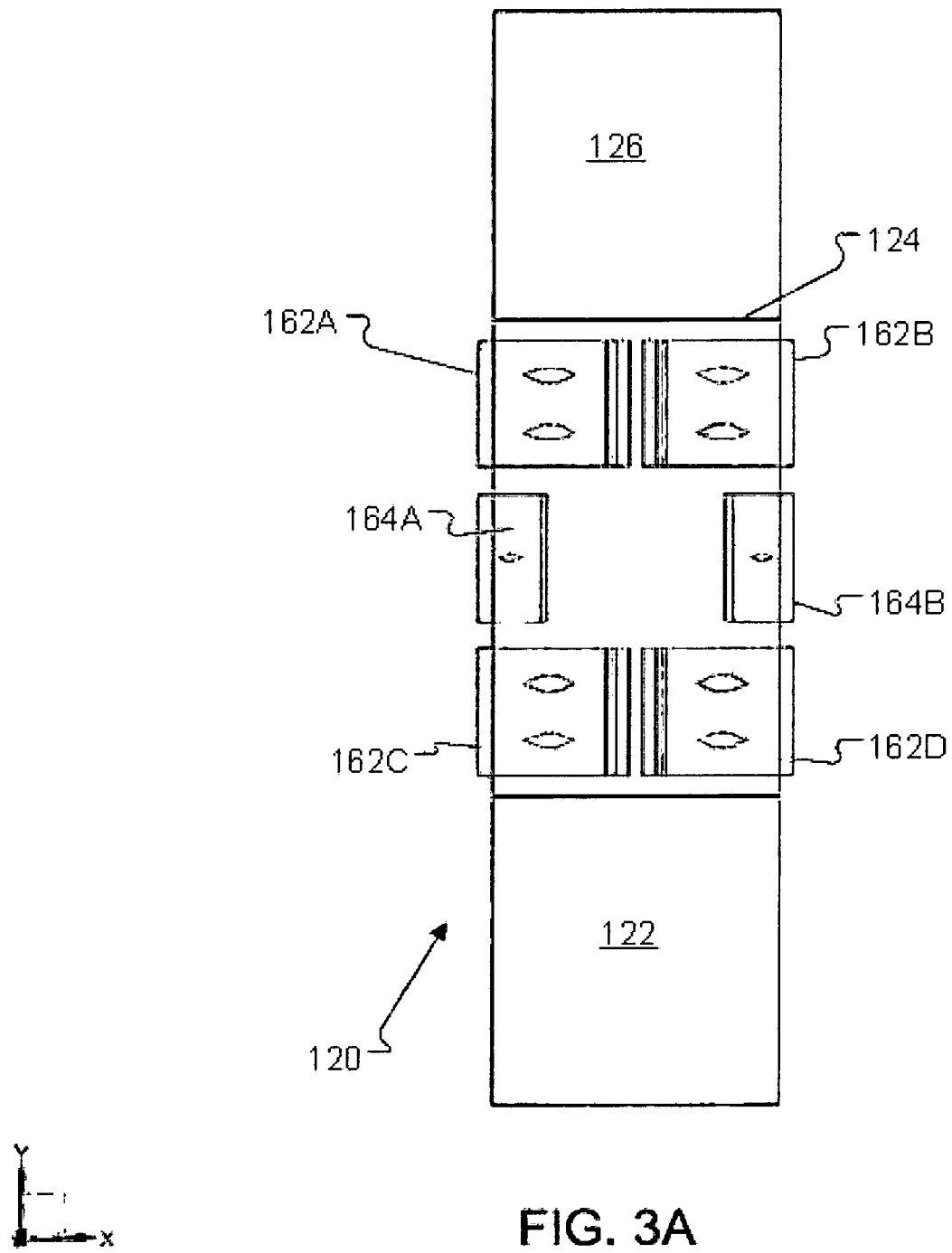
FIG. 3A is a top view of the raised floor of the system of FIG. 1A, illustrating vent duct positioning and traffic flow of vehicles, according to various embodiments.

FIG. 3A is a top view of the raised floor 120 of the system 100 of FIG. 1A, illustrating vent duct positioning and traffic flow of vehicles, according to various embodiments. A vehicle in traffic may enter up the first ramp 122 and park on top of the middle portion 124 of the raised floor 120. While the vehicle is at rest on the raised floor 120, when the one or more fan 140 is turned on, the air may flow up through the vent ducts 162A, 164A, 162B, 164B, 162C, and 162D as discussed with reference to FIG. 2A. After the screening process is complete, the vehicle may exit down the second ramp 126 and back into the flow of traffic, if there was no detection, or to a second screening area for manual search of the vehicle, if there was detection of a substance by the canine (or by other form of detection integrated into the system 100 such as x-ray or a gas-chromatograph mass-spectrometer, for example).

Figure 3B:
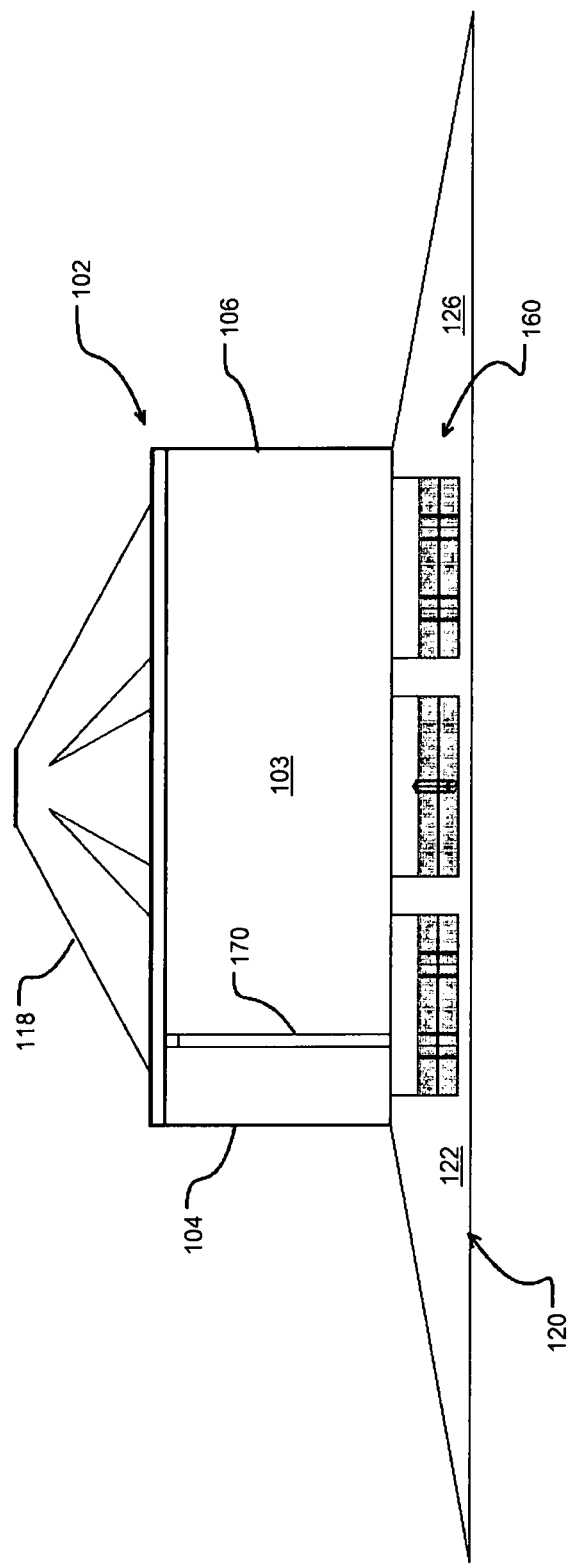
FIG. 3B is a side view of the container, with raised floor, of the system of FIG. 1A, illustrating traffic flow and an optional x-ray device according to embodiments.

FIG. 3B is a side view of the container 102, with the raised floor 120, of the system 100 of FIG. 1A, illustrating traffic flow and an optional x-ray device according to embodiments. The x-ray device 170 may be located adjacent or proximate to one of the first doors 104 or second door 106 of the container 102. In various embodiments, the x-ray device 170 may be a backscatter and/or a forward scatter type x-ray device that radiates the x-rays and detects return x-ray radiation after scattering off of the vehicle and other objects within the vehicle. When the vehicle is moving slowly (such as less than 5 miles per hour), the x-ray device 170 may scan the vehicle from multiple directions (e.g., points of view) while the vehicle enters through the first door 104 into the container 102 or exits out of the second door 106 of the container 102. The x-ray device 170 may, in this way, be an additional source of detection of contraband, drugs, firearms, trafficked humans, and the like.

FIG. 4A is a top view of the raised floor 120 of the container of FIG. 1A according to an embodiment. The first ramp 122 may lead to the entrance of the container 102 and the second ramp 126 may lead to the exit of the container 102. Illustrated are relative dimensions and placements of the vent ducts 162A, 164A, 162B, 164B, 162C, and 162D, according to one embodiment. The dimensions are in inches.

FIG. 4B is a side view of the raised floor 120 of the container of FIG. 1A according to an embodiment. The dimensions of the vent ducts 162A, 164A, 162B, 164B, 162C, and 162D correspond to those illustrated in FIG. 4A. Additionally, the slope of each of the first ramp 122 and the second ramp 126 may be approximately 10 degrees, or 17.6%, less than the widely accepted 20% maximum grade. Use of this slope may allow for quick and safe transition of vehicles through the container for screening.

FIG. 4C is a cross-section view at section C-C of the raised floor of FIG. 4B according to an embodiment. In one embodiment, the angle at which the vent ducts 164A and 164B exit into the chamber 103 is 65 degrees, as illustrated, but this angle may range between approximately 55 degrees and 70 degrees. FIG. 4D is a cross-section view at section B-B of the raised floor of FIG. 4B. In one embodiment, the angle at which the vent ducts 162A, 162B, 162C, and 162D exit into the chamber 103 is 30 degrees, as illustrated, but this angle may range between approximately 25 degrees and 40 degrees.

Figure 5A:
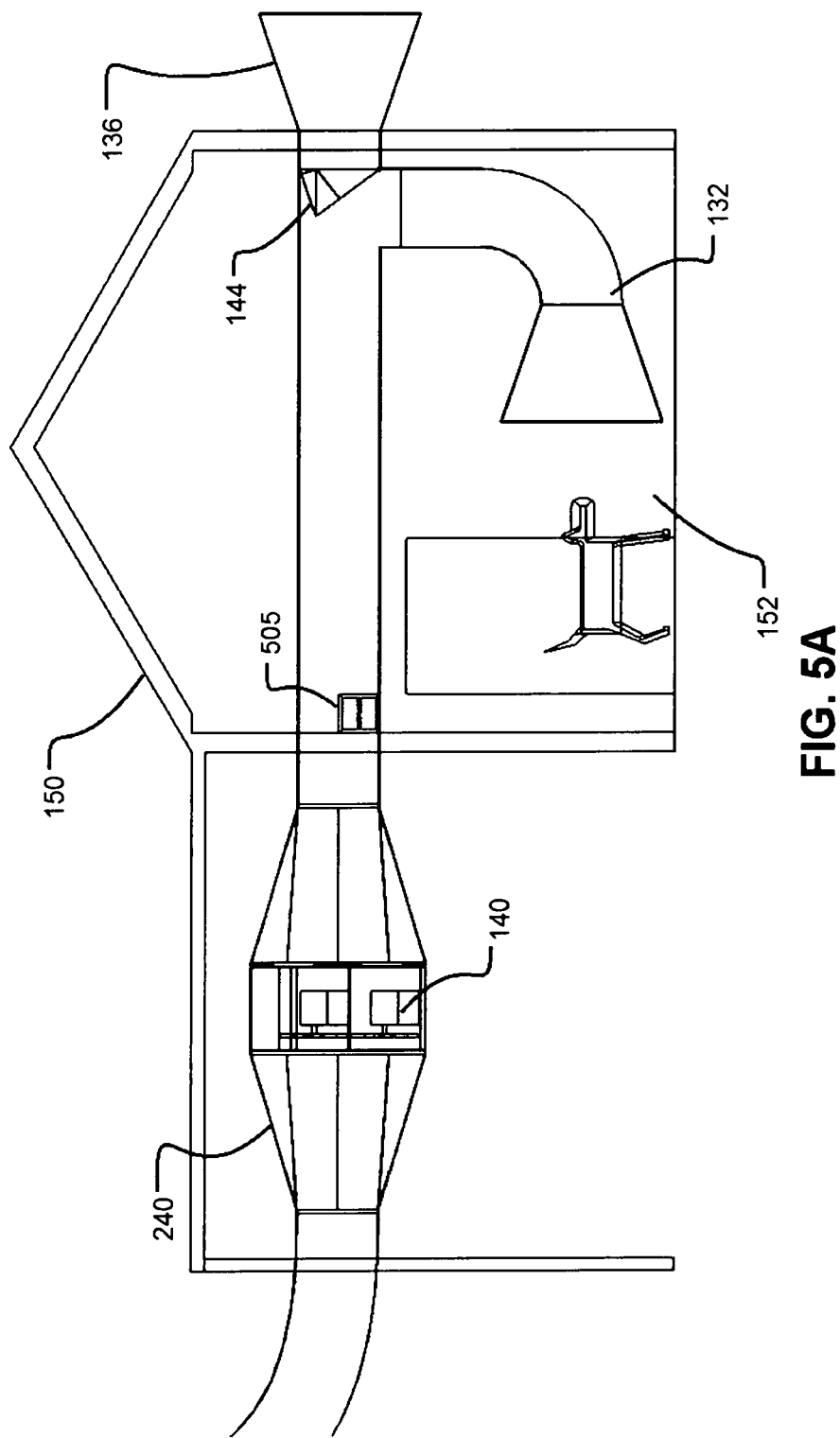
FIG. 5A is a side view of the system of FIG. 1 with an optional gas-chromatograph mass-spectrometer device located within the air duct after the one or more fan that pulls air into the canine-sniffing location according to an embodiment.

FIG. 5A is a side view of the system 100 of FIG. 1 with an optional gas-chromatograph mass-spectrometer device 505 located within the air duct 130 after the one or more fan 140 that pulls air into the canine-sniffing location 152 according to an embodiment. The gas-chromatograph mass-spectrometer device 505 may collect a sample of the air during the screening of any vehicle, but may also be employed as confirmation test in response to canine detection of an illegal substance associated with any given vehicle.

Gas chromatography-mass spectrometry (GC-MS) is an analytical method that combines the features of gas-chromatography and mass spectrometry to identify different substances within a test sample. Applications of GC-MS include drug detection, fire investigation, environmental analysis, explosives investigation, and identification of unknown samples. GC-MS can also be used in airport security to detect substances in luggage or on human beings. Additionally, it can identify trace elements in materials that were previously thought to have disintegrated beyond identification. Like liquid chromatography-mass spectrometry, it allows analysis and detection even of tiny amounts of a substance.

GC-MS has been regarded as a "gold standard" for forensic substance identification because it is used to perform a 100% specific test, which positively identifies the presence of a particular substance. A nonspecific test merely indicates that any of several in a category of substances is present. Although a nonspecific test could statistically suggest the identity of the substance, this could lead to false positive identification.

Figure 5B:
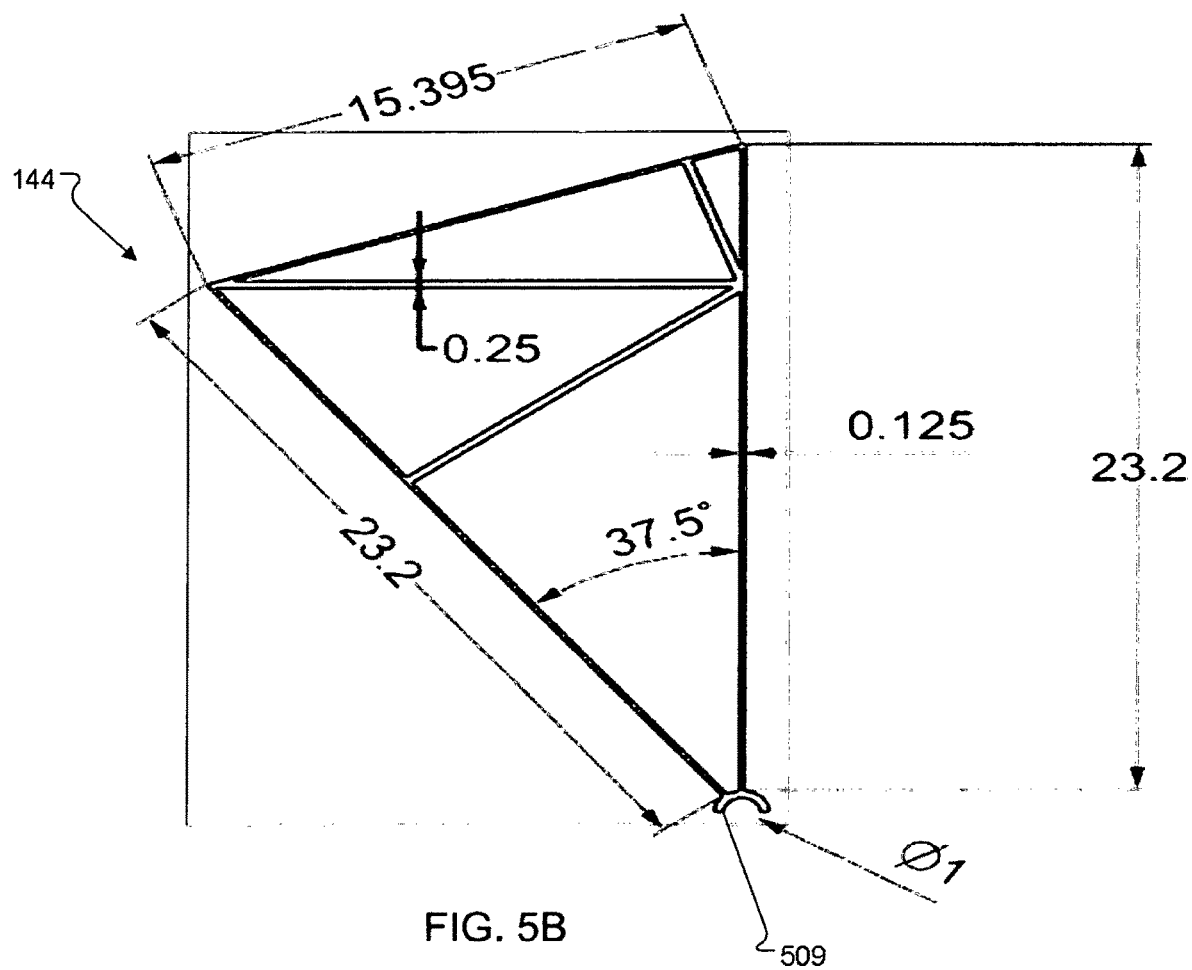
FIG. 5B is a side view of a pivotal flap employed within the distal end of the air duct according to an embodiment.

FIG. 5B is a side view of the pivotal flap 144 employed within the distal end of the air duct 130 according to an embodiment. The pivotal flap 144 illustrated may be three-dimensional, have a triangular cross-section, and pivots about a longest axis of axes formed through points of the triangular cross-section. The pivotal flap 144 may contain a half-cylindrical structure 509 for pivoting or rotating about a portion of the inside of the air duct 130 that transitions between the first portion 132 and the second portion 136 of the distal end of the air duct 130. In one embodiment, the pivotal flap 144 is designed using right triangles to optimize support of each wall and resist buckling or flexing.

Figure 5C:
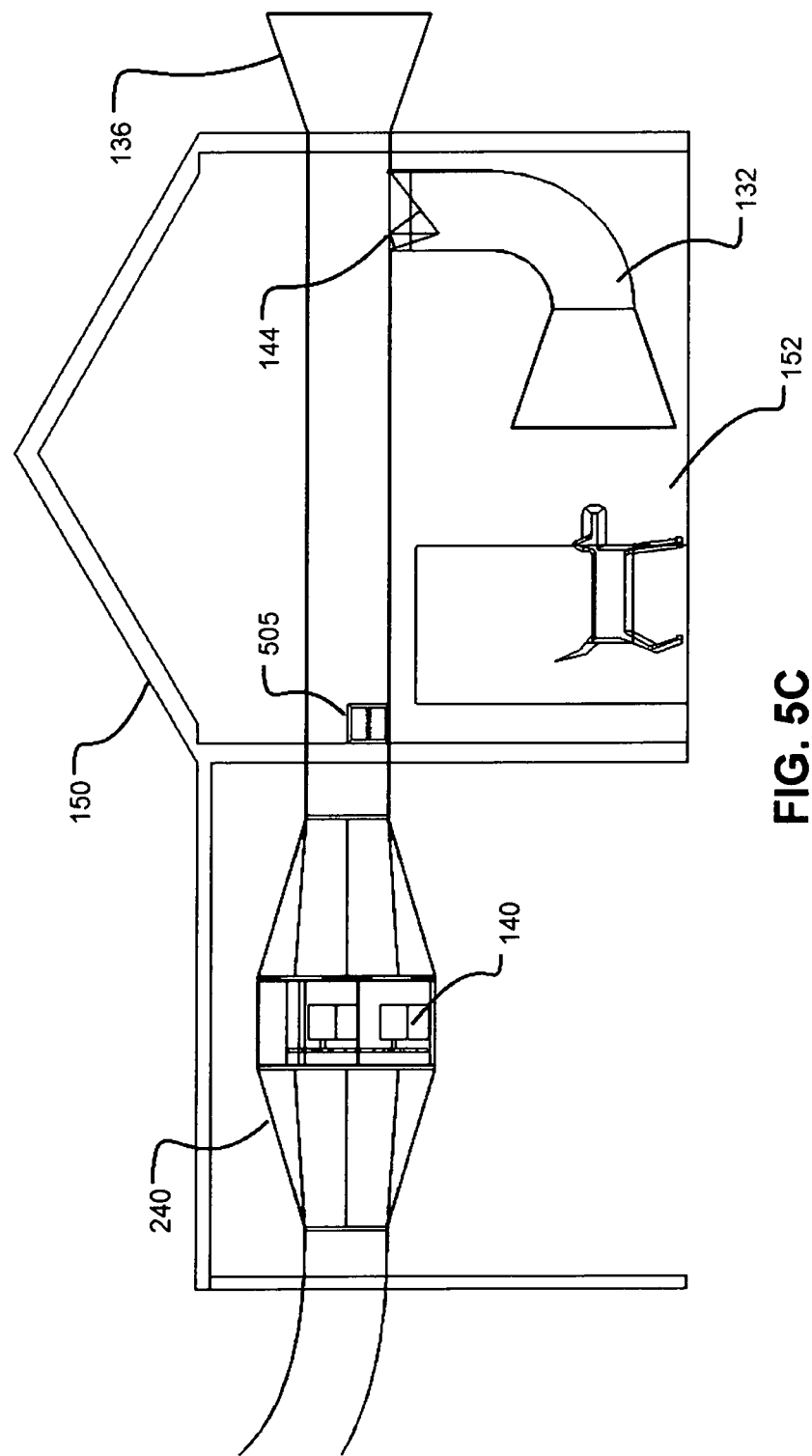
FIG. 5C is a side view of the system of FIG. 5A, illustrating the pivotal flap of FIG. 5B rotated over a first portion of the distal end of the air duct so air may be purged, through a second portion of the distal end, out of the container and air duct of the system of FIG. 1A according to an embodiment.

FIG. 5C is a side view of the system of FIG. 5A, illustrating the pivotal flap 144 of FIG. 5B rotated over the first portion 132 of the distal end of the air duct so air may be purged, through the second portion 136 of the distal end, out of the container 102 and air duct 130 of the system 100 of FIG. 1A according to an embodiment. The pivoting mechanism of the pivotal flap 144 may facilitate quick and optionally automated switching between the pivotal flap 144 closing off the first portion 132 of the distal end, e.g., during purging, or closing off the second portion 136 of the distal end, e.g., during canine detective screening for odors.

Figure 6:
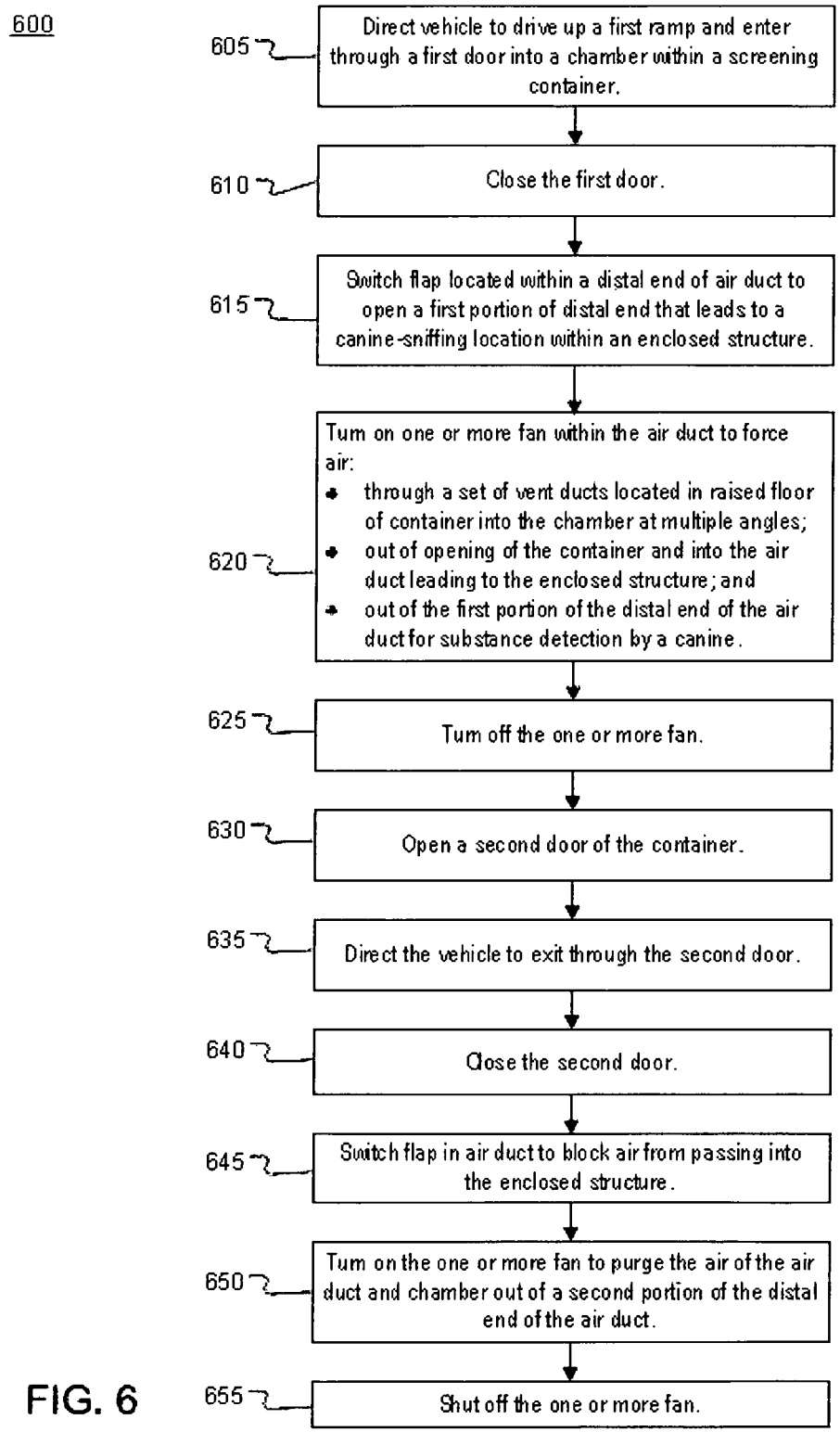
FIG. 6 is a flow chart of a method for detecting substances hidden within a vehicle with canine detection, according to various embodiments.

FIG. 6 is a flow chart of a method 600 for detecting substances hidden within a vehicle with canine detection, according to various embodiments. The method 600 may be performed by the system 100 disclosed herein and related alternative embodiments to the system 100. The method 600 may begin with directing the vehicle to drive up a first ramp and enter through a first door into a chamber within a screening container (605). The method 600 may continue with closing the first door (610). The method 600 may continue with switching a flap located within a distal end of an air duct to open a first portion of the distal end of the air duct that leads to a canine-sniffing location within an enclosed structure, wherein a proximal end of the air duct hovers over an opening within the container (615). The method 600 may continue with turning on one or more fan within the air duct to force air: through a set of vent ducts, which are located within a raised floor of the container, into the chamber of the container at multiple angles with respect to a bottom of the vehicle; out of opening of the container and into the air duct leading to the enclosed structure; and out of the first portion of the distal end of the air duct, for substance detection by a canine at the canine-sniffing location within the enclosed structure (615).

With continued reference to FIG. 6, the method 600 may continue with turning off the one or more fan (625). The method 600 may continue with opening a second door of the container (630). The method 600 may continue with directing the vehicle to exit through the second door (635). The method 600 may continue with closing the second door (640).

With continued reference to FIG. 6, the method 600 may continue with switching the flap in the air duct to block air from passing into the enclosed structure through the first portion of the distal end (645). The method 600 may continue with turning on the one or more fan to purge the air of the air duct and chamber out of a second portion of the distal end leading to outside of the enclosed structure (650). The method 600 may continue with shutting off the one or more fan in preparation for entry of a second vehicle into the container (655). In an alternative embodiment, the turning off the one or more fan (at block 625) and turning the one or more fan back on (at block 650) may be eliminated such that the chamber and the air duct are purged without stopping and starting the one or more fan. Additional changes to these steps are envisioned.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and may not necessarily have an ordinal meaning according to their numerical designation.

The above description sets forth numerous specific details such as examples of specific systems, components, methods, and so forth, in order to provide a good understanding of several embodiments. It will be apparent to one skilled in the art, however, that at least some embodiments may be practiced without these specific details. In other instances, well-known components or methods are not described in detail or are presented in simple block diagram format in order to avoid unnecessarily obscuring the present embodiments. Thus, the specific details set forth above are merely exemplary. Particular implementations may vary from these exemplary details and still be contemplated to be within the scope of the present embodiments.

It is to be understood that the above description is intended to be illustrative and not restrictive. Many other embodiments will be apparent to those of skill in the art upon reading and understanding the above description. The scope of the present embodiments should, therefore, be determined with reference to the appended claims, along with the full scope of equivalents to which such claims are entitled.

What is claimed is:

1. A system comprising: a container to enclose vehicles within a chamber to be screened for substances, wherein the container includes a first door at an entrance, a second door at an exit, and a raised floor, raised with respect to the ground, wherein the raised floor comprises:
   a first ramp leading to the first door;
   a second ramp leading to the second door; and
   two or more vent ducts enclosed within the raised floor, the vent ducts to direct air flow into the chamber of the container from outside of the chamber;
an enclosed structure to house a canine; and
an air duct comprising:
   a proximal end located proximate to an opening within a top wall of the container, the top wall being a ceiling of the container;
   a distal end fed through the enclosed structure to a canine-sniffing location, said canine-sniffing location being where a canine performs substance detection; and
   one or more fans to pull air out of the chamber and deliver the air to the canine-sniffing location within the enclosed structure.

2. The system of claim 1, wherein the one or more fans comprises three fans arranged in parallel that, together, pull between 4,800 cubic feet per minute and 21,000 cubic feet per minute of the air.

3. The system of claim 1, further comprising a diffuser attached to the distal end of the air duct that is proximate to the canine-sniffing location, the diffuser to slow the air before exiting into the enclosed structure.

4. The system of claim 3, wherein the distal end of the air duct further comprises:
   a first portion, which exits out of the enclosed structure, the first portion to purge air out of the air duct before a screening, wherein the screening is the process of delivering air from the chamber to the canine;
   a second portion that includes the diffuser; and
   a pivotal flap located between the first and second portions, the pivotal flap to switch between allowing air through one of the first portion or the second portion.

5. The system of claim 1, wherein each of the vent ducts within the raised floor includes a screen-filter combination at an opening of each of the vent ducts the screen-filter combination being configured to protect against foreign object debris from entering the chamber.

6. The system of claim 1, wherein the opening in the top wall comprises multiple openings, each of the multiple openings being in the top wall containing a grate, wherein the grates are screens, and wherein the proximal end of the air duct includes a pyramid-shaped funnel positioned over each of the grates, to funnel the air from the chamber into the air duct.

7. The system of claim 1, wherein at least a first vent duct of the two or more vent ducts exits into the chamber at approximately 30 degrees with respect to the ground, and wherein at least a second vent duct of the two or more vent ducts exits into the chamber at approximately 65 degrees with respect to the ground.

8. A system comprising:
   a container to enclose vehicles within a chamber to be screened for substances, wherein the container includes a first door at an entrance, a second door at an exit, and a raised floor, raised with respect to the ground, wherein the raised floor comprises:
      a first vent duct enclosed within the raised floor, wherein the first vent duct exits into the chamber at an angle between 25 and 40 degrees with respect to the ground; and
      a second vent duct enclosed within the raised floor, wherein the second vent duct exits into the chamber at an angle between 55 and 75 degrees with respect to the ground;
   an enclosed structure to house a canine; and
   an air duct positioned proximate to an opening within one of a side wall or a top wall of the container, and that is fed through the enclosed structure to a canine-sniffing location within the enclosed structure, wherein the canine-sniffing location is configured to contain a canine that performs substance detection, and wherein a first end of the air duct is pyramid-shaped to funnel the air of the chamber into the air duct.

9. The system of claim 8, further comprising an X-ray device attached to upper sides of the chamber near one of the first door or the second door, the X-ray device adapted to scan the vehicle as the vehicle moves into or out of the container.

10. The system of claim 8, further comprising:
    one or more fans to pull air out of the chamber and deliver the air to the canine-sniffing location within the enclosed structure; and
    a diffuser attached to a second end of the air duct leading to the canine-sniffing location, the diffuser to slow the air before exiting into the enclosed structure.

11. The system of claim 10, further comprising a gas-chromatograph mass-spectrometer device attached to an inside of the air duct between the one or more fans and the diffuser.

12. The system of claim 8, wherein a distal end of the air duct comprises:
    a first portion, which exits out of the enclosed structure, the first portion configured to purge air out of the air duct before a screening, wherein the screening is the process of delivering air from the chamber to the canine;
    a second portion that exits to the canine-sniffing location; and
    a pivotal flap located between the first and second portions, the pivotal flap to switch between allowing air through one of the first portion or the second portion.

13. The system of claim 12, wherein the pivotal flap is three-dimensional, has a triangular cross-section, and pivots about a longest axis of axes formed through points of the triangular cross-section.

14. The system of claim 8, wherein the raised floor further comprises:
    a third vent duct enclosed within the raised floor, wherein the third vent duct exits into the chamber at an angle between 25 and 40 degrees, with respect to the ground, and is positioned across the chamber from the first vent duct symmetrically reflected across the longest axis of axes of the raised floor;
    a fourth vent duct enclosed within the raised floor, wherein the fourth vent duct exits into the chamber at an angle between 55 and 75 degrees, with respect to the ground, and is positioned across the chamber from the second vent duct symmetrically reflected across the longest axis of axes of the raised floor;
    a first ramp leading to the entrance; and
    a second ramp leading to the exit.

15. The system of claim 14, wherein each of the first, second, third, and fourth vent ducts includes a screen-filter combination at an opening of each one of the vent ducts to the side wall of the raised floor to protect against foreign object debris from entering the chamber by limiting the size of particles or objects which can pass through, and wherein the opening in the top wall comprises multiple openings, each of the openings in the top wall containing a grate.

16. A method for detecting substances hidden within a vehicle, the method comprising:

directing the vehicle to drive up a first ramp and enter through a first door into a chamber within a container which houses the vehicle for a screening, wherein the screening is the process of delivering air from the chamber to a canine which analyzes the air for substances;

closing the first door;

switching a pivotal flap located within a distal end of an air duct, wherein the distal end of the air duct delivers air to the canine and the flap pivots to change the direction of air flow, to open a first portion of the distal end of the air duct that leads to a canine-sniffing location, wherein a canine performs substance detection, within an enclosed structure which houses the canine, wherein a proximal end of the air duct hovers over an opening within the container to direct air flow from the container to the distal end of the air duct; and turning on one or more fans within the air duct to force air:

through one or more vent ducts, which are located within a raised floor of the container with the purpose of directing air from outside of the raised floor into the container, and wherein the raised floor is raised with respect to the ground, where the air is then directed into the chamber of the container at multiple angles with respect to the ground;

out of the opening of the container and into the air duct leading to the enclosed structure; and out of the first portion of the distal end of the air duct, for substance detection by a canine at the canine-sniffing location within the enclosed structure.

17. The method of claim 16, further comprising scanning the vehicle with an X-ray device as the vehicle one of enters or exits the container, to obtain X-ray imaging of the vehicle from multiple directions.

18. The method of claim 16, further comprising collecting a sample of the air for testing by a gas-chromatograph mass-spectrometer device attached to an inside of the air duct between the one or more fans and the distal end of the air duct.

19. The method of claim 16, further comprising:

turning off the one or more fans;

opening a second door of the container;

directing the vehicle to exit through the second door; and closing the second door.

20. The method of claim 19, further comprising:

switching the flap in the air duct to block air from passing into the enclosed structure through the first portion of the distal end;

turning on the one or more fans to purge the air of the air duct and the chamber out of a second portion of the distal end leading to outside of the enclosed structure; and shutting off the one or more fans in preparation for entry of a second vehicle into the container.

* * * * *